United States Patent
Driemel

(10) Patent No.: US 9,285,440 B2
(45) Date of Patent: Mar. 15, 2016

(54) SIZE-ADJUSTABLE HEAD/NECK MR SURFACE COIL WITH HINGED UPPER SECTION

(75) Inventor: Daniel Driemel, Oederan (DE)

(73) Assignee: Siemens Aktiengesellschaft, München (DE)

(*) Notice: Subject to any disclaimer, the term of this patent is extended or adjusted under 35 U.S.C. 154(b) by 838 days.

(21) Appl. No.: 13/464,911

(22) Filed: May 4, 2012

(65) Prior Publication Data

US 2012/0286784 A1    Nov. 15, 2012

(30) Foreign Application Priority Data

May 6, 2011 (DE) .......................... 10 2011 075 454

(51) Int. Cl.
*G01R 33/34* (2006.01)
*A61B 5/055* (2006.01)

(52) U.S. Cl.
CPC .......... *G01R 33/34007* (2013.01); *A61B 5/055* (2013.01); *G01R 33/34084* (2013.01)

(58) Field of Classification Search
CPC ................... G01R 33/34007; G01R 33/34084; A61B 5/055
See application file for complete search history.

(56) References Cited

U.S. PATENT DOCUMENTS

| | | | | |
|---|---|---|---|---|
| 5,166,618 A * | 11/1992 | Jones et al. | ............. | 324/318 |
| 5,185,577 A * | 2/1993 | Minemura | ............. | 324/318 |
| 5,221,902 A * | 6/1993 | Jones et al. | ............. | 600/422 |
| 5,261,403 A * | 11/1993 | Saito et al. | ............. | 600/422 |
| 5,307,806 A | 5/1994 | Jones | | |
| 5,361,765 A * | 11/1994 | Herlihy et al. | ............. | 600/422 |
| 5,370,118 A * | 12/1994 | Vij et al. | ............. | 600/422 |
| 5,435,302 A * | 7/1995 | Lenkinski et al. | ............. | 600/422 |
| 5,517,120 A * | 5/1996 | Misic et al. | ............. | 324/318 |
| 5,952,830 A * | 9/1999 | Petropoulos et al. | ......... | 324/318 |
| 6,037,773 A | 3/2000 | Mitsumata et al. | | |
| 6,137,291 A * | 10/2000 | Szumowski et al. | ......... | 324/318 |
| 6,316,941 B1 * | 11/2001 | Fujita et al. | ............. | 324/318 |
| 6,441,612 B1 * | 8/2002 | Shimo et al. | ............. | 324/309 |
| 6,980,002 B1 * | 12/2005 | Petropoulos et al. | ......... | 324/318 |
| 7,098,660 B2 * | 8/2006 | Contrada et al. | ............. | 324/318 |
| 7,288,938 B2 * | 10/2007 | Chmielewski et al. | ....... | 324/318 |
| 7,394,256 B2 * | 7/2008 | Schubert et al. | ............. | 324/321 |
| 2007/0152667 A1 | 7/2007 | Schubert et al. | | |

FOREIGN PATENT DOCUMENTS

| | | |
|---|---|---|
| DE | 103 14 215 B4 | 11/2006 |
| DE | 10 2006 027 189 A1 | 12/2007 |
| JP | 2001095776 A | 4/2001 |

OTHER PUBLICATIONS

German Office Action dated Feb. 3, 2012 for corresponding German Patent Application No. DE 10 2011 075 454.7 with English translation.

German Office Action dated Jan. 7, 2014 for corresponding German Patent Application No. DE 10 2011 075 454.7 with English translation.

* cited by examiner

*Primary Examiner* — Dixomara Vargas
(74) *Attorney, Agent, or Firm* — Lempia Summerfield Katz LLC

(57) ABSTRACT

A local coil for a magnetic resonance tomography system includes an upper section and a lower section. The upper section is hingeable in relation to the lower section.

23 Claims, 7 Drawing Sheets

SIZE-ADJUSTABLE HEAD/NECK MR SURFACE COIL WITH HINGED UPPER SECTION

This application claims the benefit of DE 10 2011 075 454.7, filed on May 6, 2011.

BACKGROUND

The present embodiments relate to a magnetic resonance tomography (MRT) local coil for an MRT system.

Magnetic resonance tomography devices for examination of objects or patients by magnetic resonance tomography (e.g., MRT, MRI, MR) are known, for example, from DE10314215B4.

In MR tomography, images with a high signal-to-noise ratio (SNR) may be recorded with coils or local coils. The coils or local coils are antenna systems that are attached in the immediate vicinity on (e.g., anterior) or below (e.g., posterior) the patient. In an MR measurement, excited nuclei (e.g., in a recording area in the object under examination) induce voltages in each case in the individual antennas of the local coil. The induced voltages are amplified with a low-noise preamplifier (e.g., LNA, Preamp) and are transferred via a cable, for example, to receive electronics. To improve the signal-to-noise ratio, even in high-resolution images, for example, high field systems are used as MRTs (e.g., 1.5 T to 12 T and more). Since more individual antennas may be connected to an MRT receive system than there are receivers present, a switching matrix (e.g., an RCCS) is installed between receive antennas and receivers. This routes the currently active receive channels (e.g., the receive channels that lie right in the field of view (FoV) of the magnet/MRT) onto the available receivers. More coil elements than there are receivers present may be connected, since for whole body coverage, only the coil elements that are located in the FoV and/or in the homogeneity volume of the magnet of the MRT are to be read out.

"Coil" (e.g., local coil) refers to an antenna system (e.g., an array coil) that may include one or more antenna elements (e.g., coil elements). The individual antenna elements may be embodied as loop antennas (e.g., loops) or butterfly coils. A coil includes coil elements, a preamplifier, further electronics (e.g., sheath wave filters) and cabling, the housing and, for example, a cable with a plug connector, through which the coil is connected to the MRT system. A receiver (RX) attached to the system side filters and digitizes signals received from the local coil and transfers generated data based thereon to a digital signal processor. The digital signal processor may derive an image or a spectrum from the measurement and makes the image or the spectrum available to the user for diagnosis.

To achieve a high SNR, the antenna elements are attached as close as possible to the patient contour of the patient to be examined. The interior space of an MR head coil may be small, for example. This is provided for high-channel coils, of which the smaller antenna elements possess a smaller optimal penetration depth than other local coils (e.g., with fewer coil elements).

One objective is, despite a smaller coil interior space, to achieve the greatest possible patient coverage (e.g., suitability for 80-95% of patients). The face and chest area of a patient exhibits a large variance. This provides that neck coils resting closely on the patient collide at a steeply rising neck-chest transition of the patient with the chest and are thereby not able to be used. Collisions with the chin of the patient or with the nose are also possible.

This may occur with stoutly built patients with a large-volume upper back part, since when these patients lay down, the head falls into the nape of the neck, and the chin is located at a relatively high position in the coil. This leads to the upper part of the head coil (e.g., also the head/neck coil upper section) not being able to be closed as desired. The forehead area is less problematic because of the smaller variance. The height differences are around 1-2 cm, whereas differences arise in the nose area of 2-3 cm, and in the chin and chest area of more than 5 cm. The width of the head coil is less problematic because of the almost constant shape of the head.

Known head coils or head and neck coils have fixed, non-size-adjustable housings and are dimensioned, depending on design and customer requirement, to achieve 80%-95% patient coverage.

This provides that SNR is "given away" at different points because the coils are dimensioned for slightly larger heads. Sufficient space is held in reserve in the nose, chin and upper chest area because of the greater variance in this area.

A size-adjustable head coil is described in patent application DE102006027189A1, which, for example, may move a head coil upper part in the back of the head-forehead area (e.g., the y direction). This helps to increase the space for chin and nose and also increases the distance of the antenna from the forehead and the front area of the skull.

SUMMARY

The present embodiments may obviate one or more of the drawbacks or limitations in the related art. For example, a magnetic resonance tomography local coil may be further optimized.

In an alternative way to coils currently used, the present embodiments make it possible to use the coil on patients with different shaped heads.

DETAILED DESCRIPTION OF THE DRAWINGS

Figure 7:
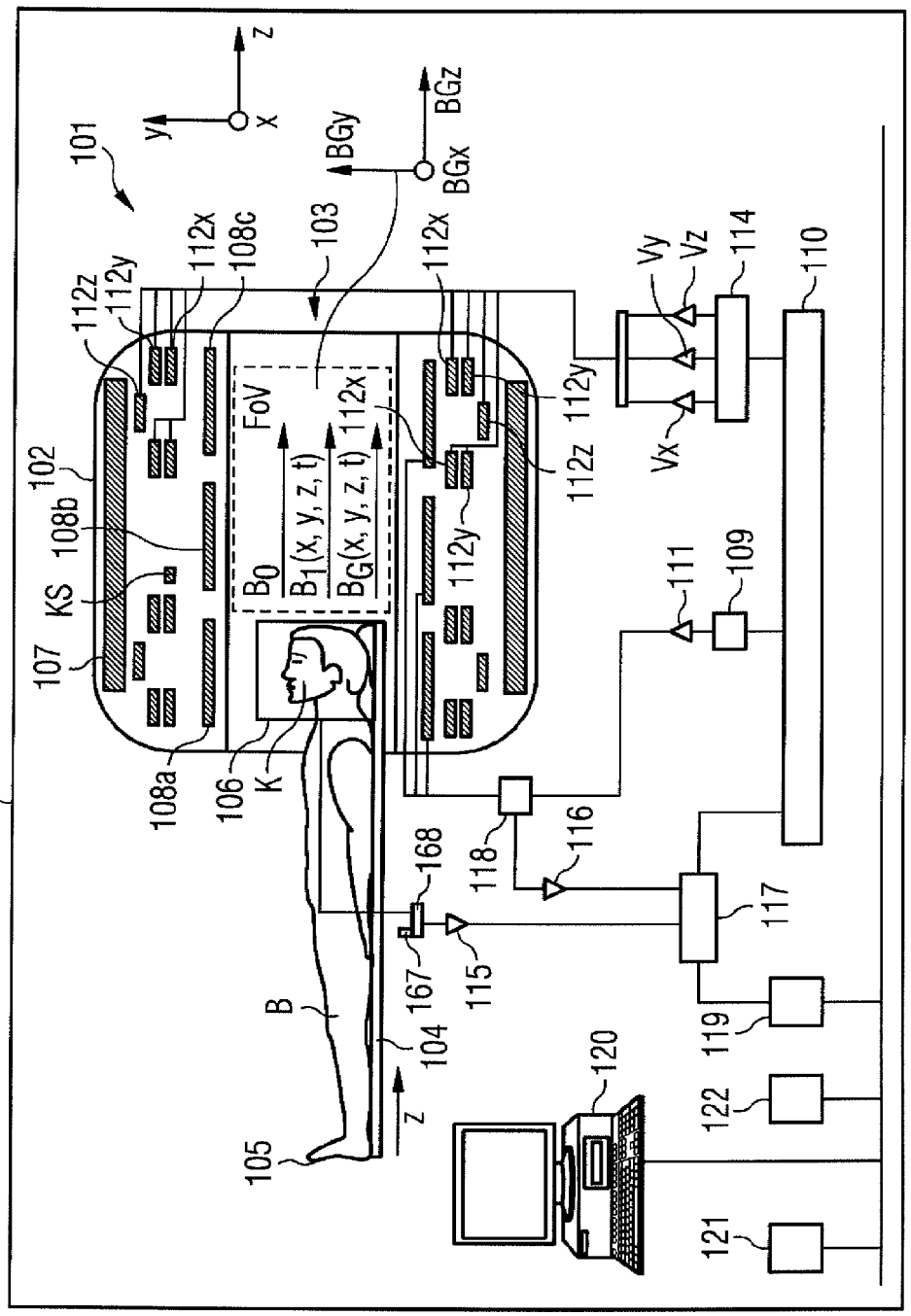
FIG. 7 shows a schematic of a magnetic resonance tomography device.

FIG. 7 shows an imaging magnetic resonance tomography (MRT) device 101 (e.g., located in a shielded room or Faraday cage F) with a whole-body coil 102 having, for example, a tubular-shaped space 103, in which a patient bed 104 with a body 105 (e.g., of an object under examination such as a patient; with or without a local coil arrangement 106) is moved in the direction of the arrow z in order to generate images of the patient 105 through an imaging process. Arranged on the patient 105, for example, is the local coil arrangement 106 (e.g., a head coil or a head-neck coil), with which, in a local area (e.g., a field of view (FOV)) of the MRT device 101, images of a part area (e.g., K) of the body 105 may be generated in the FOV. Signals of the local coil arrangement 106 may be evaluated by an evaluation device (e.g., including 168, 115, 117, 119, 120, 121) of the MRT device 101 able to be connected via coaxial cable or wirelessly (e.g., element 167) to the local coil arrangement 106 (e.g., converted into images, stored or displayed).

In order to examine the body 105 (e.g., an object under examination or a patient) with the MRT device 101 using magnetic resonance imaging, different magnetic fields matched as precisely as possible to one another in temporal and spatial characteristics are irradiated onto the body 105. A strong magnet (e.g., a cryomagnet 107) in a measurement compartment (e.g., with a tunnel-shaped opening 103) generates a static strong main magnetic field $B_0$ amounting, for example, to between 0.2 Tesla and 3 Tesla or even more. The body 105 to be examined is supported on a patient bed 104 and moved into a somewhat homogeneous area of the main magnetic field B0 in the FoV. The nuclear spin of atomic nuclei of the body 105 is excited by magnetic high-frequency excitation pulses B1 (x, y, z, t) that are beamed in via a high-frequency antenna shown in FIG. 7 in a simplified form as a body coil 108 (e.g., a multipart body coil 108a, 108b, 108c; and/or if necessary, a local coil arrangement). High-frequency excitation pulses are generated, for example, by a pulse generation unit 109 that is controlled by a pulse sequence control unit 110. After amplification by a high-frequency amplifier 111, the high-frequency excitation pulses are conveyed to high-frequency antennas 108. The high-frequency system shown in FIG. 7 is depicted schematically. In some embodiments, more than one pulse generation unit 109, more than one high-frequency amplifier 111 and a number of high-frequency antennas 108 a, b, c are used in a magnetic resonance device 101.

The magnetic resonance device 101 has gradient coils 112x, 112y, 112z, with which magnetic gradient fields are beamed in during a measurement for selective slice excitation and for local encoding of the measurement signal. The gradient coils 112x, 112y, 112z are controlled by a gradient coil control unit 114 that, like the pulse generation unit 109, is connected to the pulse sequence control unit 110.

Signals sent out by the excited nuclear spin (of the atomic nuclei in the object under examination) are received by the body coil 108 and/or by at least one local coil arrangement 106, amplified by assigned high-frequency amplifiers 116/115 and processed further and digitized by a receive unit 117. The recorded measurement data is digitized and stored as complex numerical values in a k-space matrix. An associated MR image may be reconstructed from the k-space matrix occupied by digital values using the multidimensional Fourier transformation.

For a coil that may be operated both in transmit mode and also in receive mode (e.g., the body coil 108 or a local coil 106), the correct signal forwarding is controlled by an upstream transceiver branch 118.

An image processing unit 109 creates an image from the measurement data that is displayed via an operator console 120 to a user and/or stored in a memory unit 121. A central processing unit 122 controls the individual system components.

In MR tomography, images with a high signal-to-noise ratio (SNR) are recorded with local coil arrangements. The local coil arrangements are antenna systems that are attached in the immediate vicinity on (anterior) or below (posterior), on, or in the body 105. During an MR measurement, the excited nuclei induce a voltage in the individual antennas of the local coil. The induced voltage is amplified with a low-noise preamplifier (e.g., LNA, Preamp) and forwarded to the receive electronics. To improve the signal-to-noise ratio even with high-resolution images, high field systems are used (e.g., 1.5 T and more). If more individual antennas may be connected to an MR receive system than there are receivers present, a switching matrix (e.g., an RCCS) is installed between receive antennas and receivers, for example. This routes the currently active receive channels (e.g., the receive channels that are directly in the FoV of the magnet) to the available receivers. More coil elements may be connected than there are receivers available, since, with whole-body coverage, only the coils that are located in the FoV or in a homogeneity volume of the magnet are read out.

In one embodiment, an antenna system that may, for example, consist of one element or as an array coil of a number of antenna elements (e.g., coil elements) is referred to as a local coil arrangement 106. The individual antenna elements are configured, for example, as loops or butterfly coils. A local coil arrangement may, for example, include coil elements, a preamplifier, further electronics (e.g., sheath wave filters), a housing, supports and a cable with plug connector, through which the local coil arrangement is connected to the MRT system. A receiver 168 attached to the system side filters and digitizes a signal received from a local coil 106 (e.g., wirelessly) and transfers the data to a digital signal processing device that, from the data obtained by a measurement, may derive an image or a spectrum and provides the image or the spectrum to the user (e.g., for subsequent diagnosis and/or storage by the user).

Exemplary embodiments of the MRT local coils of the present embodiments are described in greater detail below with reference to FIGS. 1-6.

Figure 1:
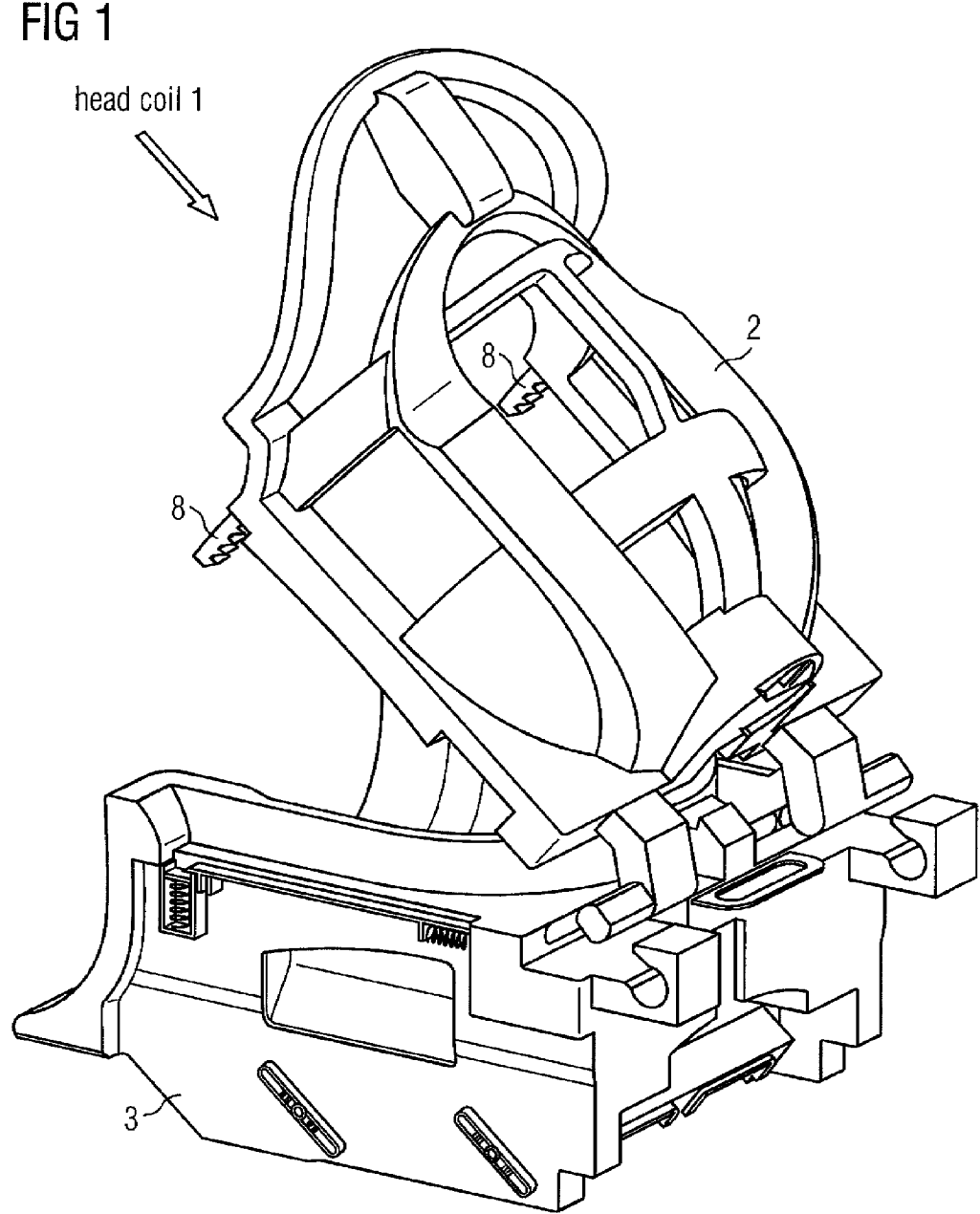
FIG. 1 shows a perspective diagram of one embodiment of a head coil as a local coil with a lower section and a removable upper section hingeable relative to the lower section.

FIG. 1 shows a schematic of one embodiment of a local coil 106 (e.g., a "head coil" in the form of a head-neck coil). A version of the local coil as a head coil (e.g., without imaging the neck) is also possible.

An upper section 2 of the head-neck coil 1 is embodied to allow the upper section 2 to be hinged relative to a lower section 3 of the local coil. In a rear area of the object under examination (e.g., cranial-terminal is a location above the head that is furthest away from the feet) and of the local coil, a hinge 4 with introduction surfaces 5 is located on the lower section 3.

Figure 2:
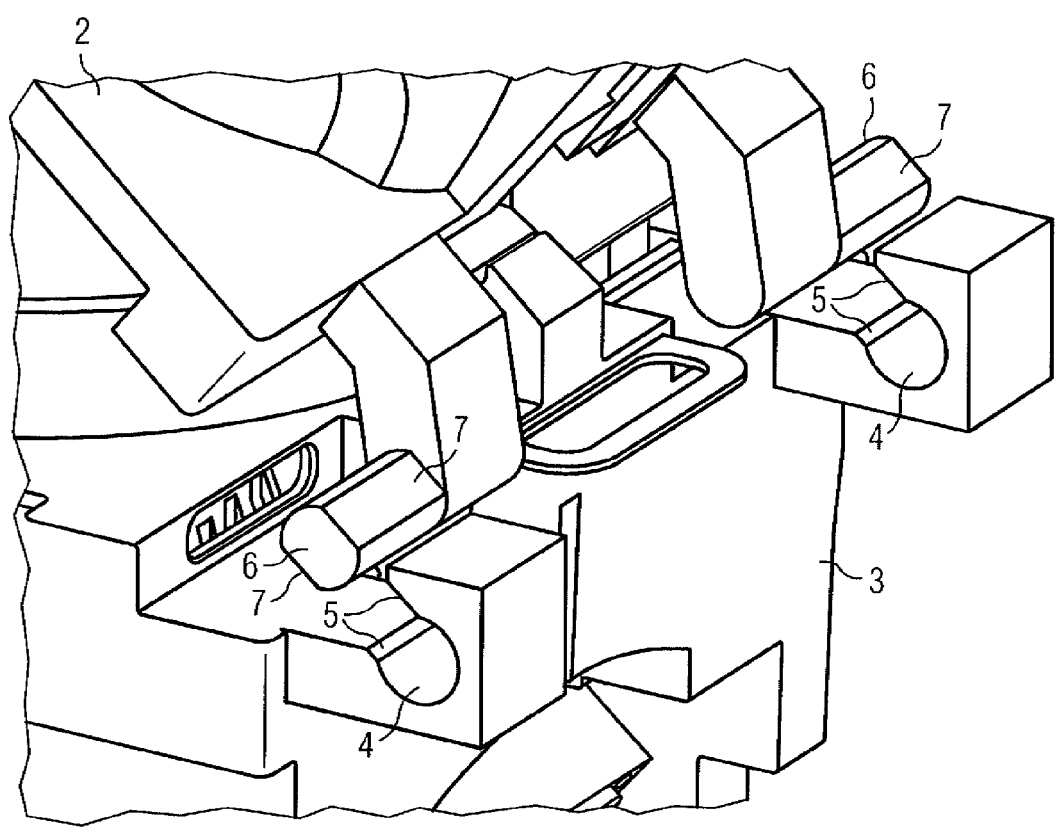
FIG. 2 shows a perspective enlarged diagram of one embodiment of a hinging mechanism on the lower section and the upper section of one embodiment of the head coil from FIG. 1 for hinging open the upper section.
Figure 3:
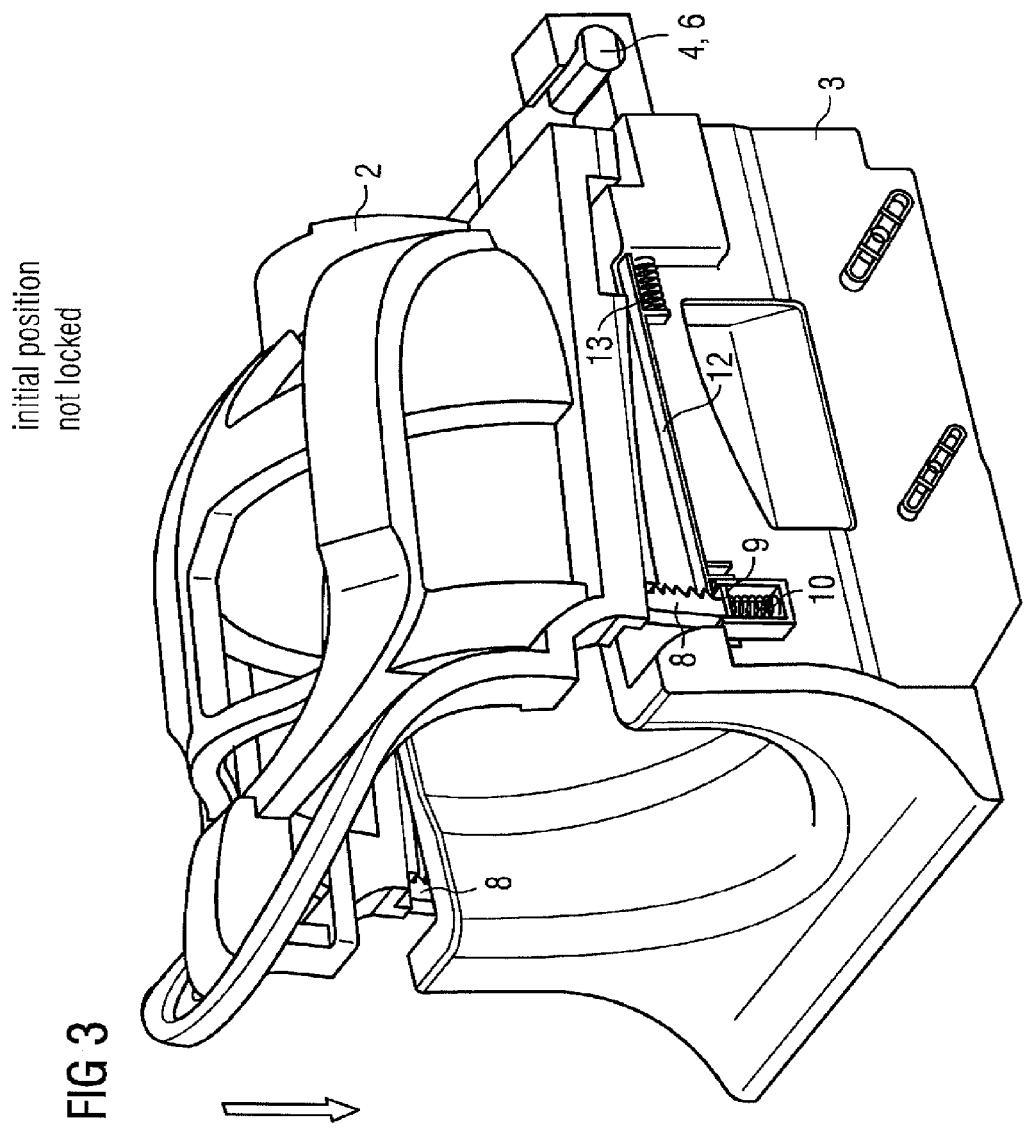
FIG. 3 shows a perspective diagram of one embodiment of a head coil with a lower section and an unlocked upper section hingeable upwards relative to the lower section, a hinging mechanism, springing and a latching device.

In the enlarged section of the coil from FIG. 1 shown in FIG. 2, a shaft 6 (e.g., a predominantly slightly cylindrical longitudinal shaft) is attached to the upper section 2 of the coil 1. The upper section 2 includes two parallel (introduction) surfaces 7 (e.g., at ends or end-side studs). The surfaces 7, in conjunction with introduction surfaces 5 in the hinged joint area of the lower section 3, provide that the upper section 2 may only be adapted to the lower section 3 or placed on the lower section 3 at a specific angle or range of angles (e.g., in a wide-opened state of the local coil having an angle >45°, >65° or >80°) in order to avoid the upper section 2 touching the patient (e.g., in the face) when the upper section 2 is placed on the lower section 3.

After the insertion of, for example, the shaft 6 or the two studs 6 of the upper section 2 into cutouts of the hinged joint 4 on the lower section 3, the shaft 6 or the studs 6 of the upper section 2 may turn in the hinged joint 4 (e.g., in the cutouts forming the hinged joint in the lower section 3), and the upper section 2 may be hinged in the direction of the patient head K and/or of the lower section 3. Latching bars 8 visible in FIG. 3, attached on both sides to the upper section 2 meet and/or rest on plates 9 supported (e.g., by pressure springs 10) on the lower section 3.

The pressure springs 10 are dimensioned so that the pressure springs 10 reliably bear the load of the upper section 2. The pressure springs 10 support an adjustment of the upper section 2 from the largest to the smallest interior space within the local coil and vice versa. This is advantageous for moving closer to the patient contour (surface) in stages and avoids the upper section of the local coil touching the patient.

Figure 4:
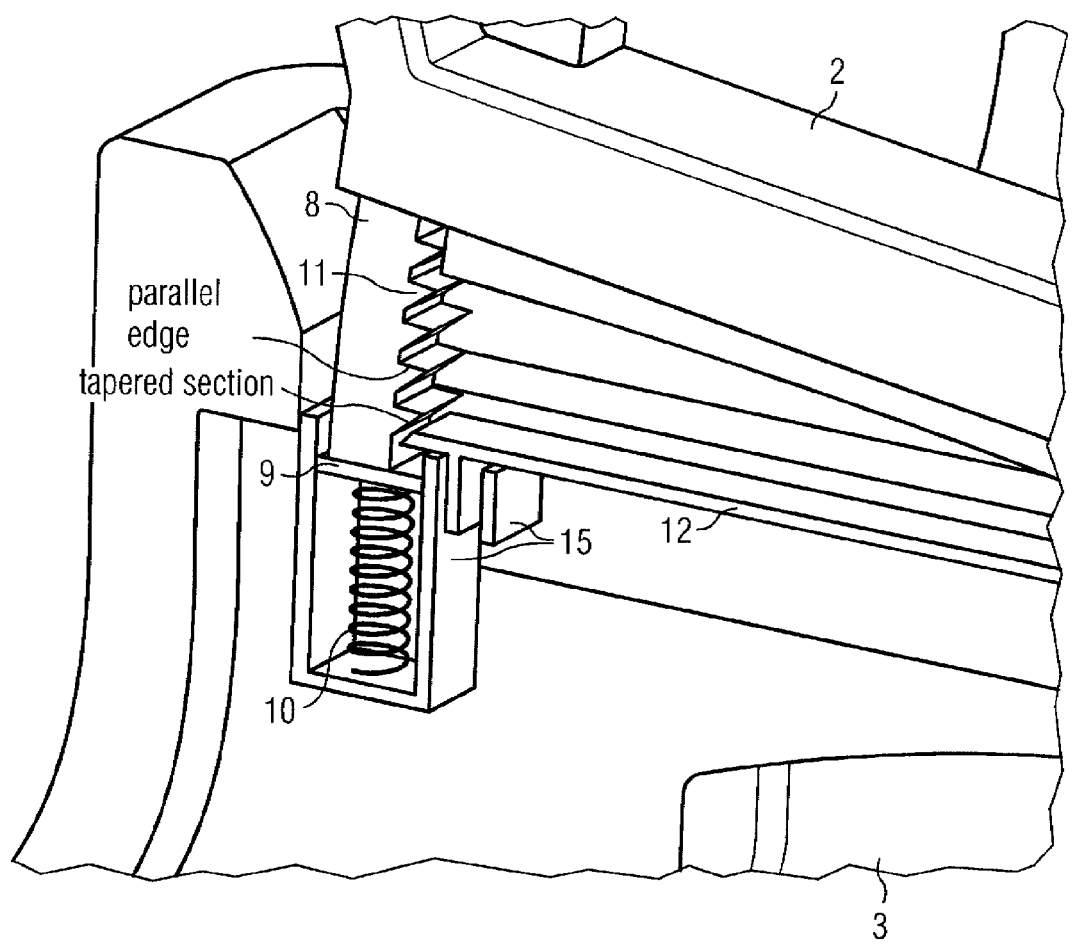
FIG. 4 shows a perspective and enlarged diagram of one embodiment of a springing device and a latching device from FIG. 3.

After the upper section 2 has been hinged down onto the lower section 3, the operator presses on the upper section 2 until (at least) a first latching edge 11 (or latching tooth) of the latching bar 8 visible in FIG. 4 displaces a locking plate 12 by tapered sections. Pressure springs 13 on both sides, after the taper has passed the first latching tooth, cause the taper to latch into a locking plate 12 (e.g., with a backwards movement).

The toothing is embodied as a saw tooth in order, through the tapered section, to reduce the adjustment force for the user and after latching (e.g., where a latching edge parallel to the locking plate 12 becomes effective/rests against the locking plate 12), to obtain a firm locking that may not be opened inadvertently by a force (e.g., a small force) exerted upwards (e.g., by the patient).

Instead of being set slightly parallel, this edge may alternatively also be set at a slight angle to allow an emergency unlocking by the patient (e.g., as a panic reaction). The angle of the angled position of this edge may define the desired unlocking force.

Figure 5:
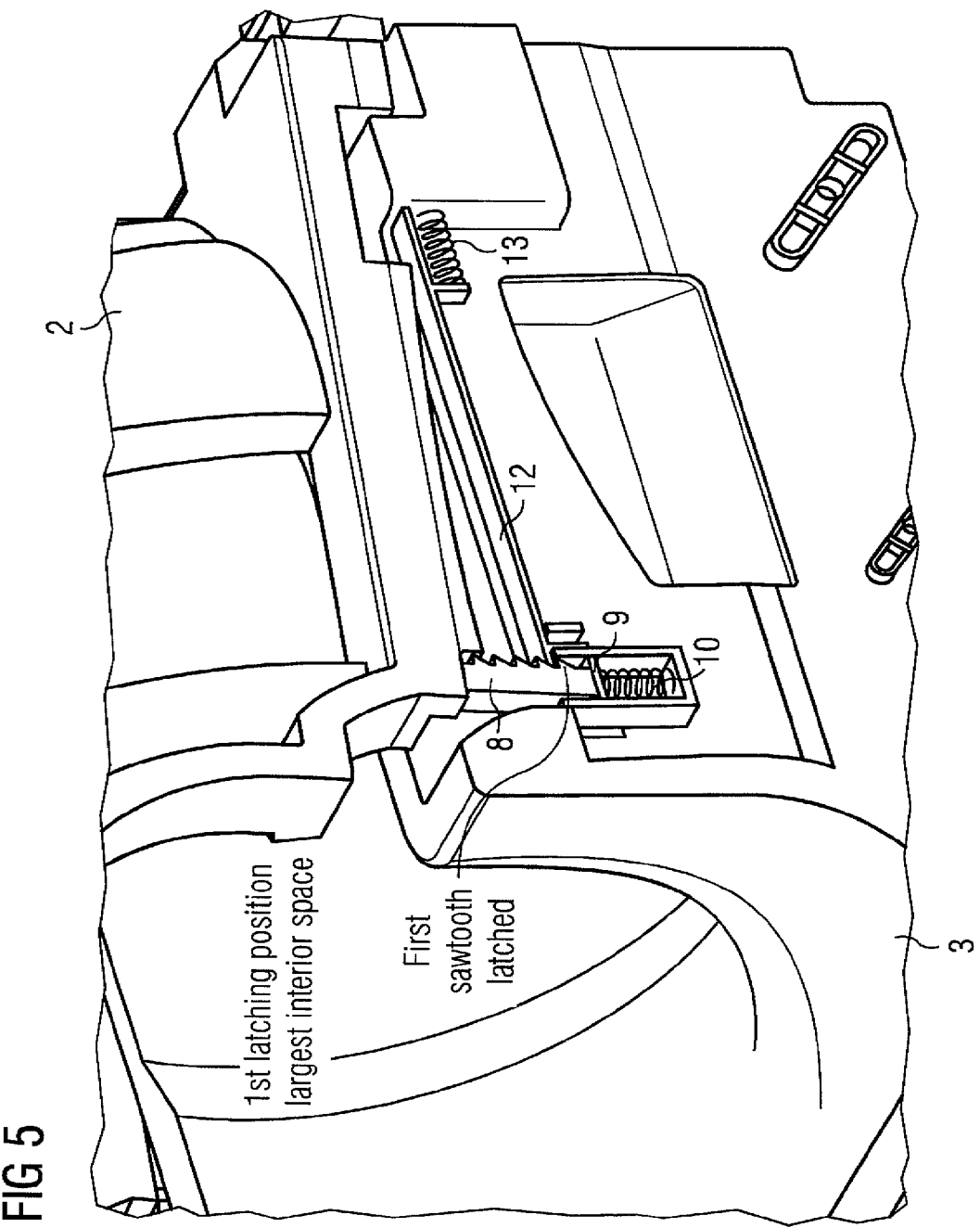
FIG. 5 shows one embodiment of a local coil in a first latching position with relatively largest local coil interior space in a latched, slightly closed state.

After a first latching (after the upper section 2 has been placed on the lower section 3) of the locking plate 12 (e.g., below a latching edge), a first and largest possible operational position (e.g., a maximum interior space of the local coil) of the local coil is reached in accordance with FIG. 5. By further pressure on the upper section 2 (e.g., in the direction of the lower section 3), the interior space of the local coil may be reduced step-by-step until a minimal patient distance (e.g., a distance between the upper section 2 and the patient) is reached.

Figure 6:
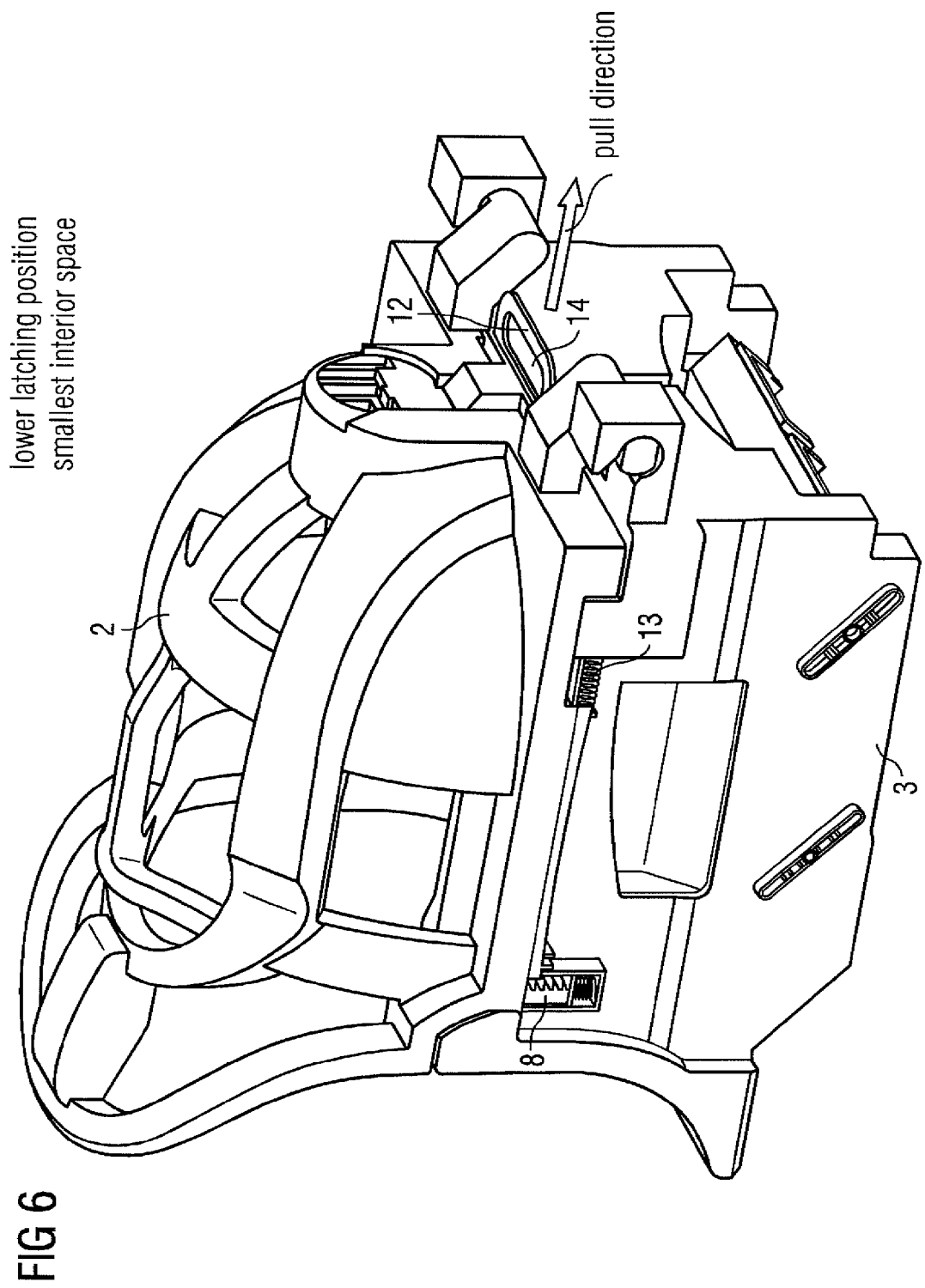
FIG. 6 shows one embodiment of a local coil in a further latched position with relatively smallest local coil interior space in a maximum closed/latched state.

To open the upper section 2, an operator grips a pull handle 14 of the locking plate 12 visible in FIG. 6 and pulls the pull handle 14 backwards (e.g., pulling in a direction away from the lower section 3). A stop 15 limits the travel in as far as only the toothing (e.g., on the at least one latching bar 8 and locking plate 12) is released. The sprung pressure plates 9 push the upper section 2 upwards into a non-locked initial position. The operator hinges the upper section 2 further up until surfaces (e.g., surfaces 5 and 7) are parallel, and the upper section 2 may be removed from the lower section 3.

The hingeable upper section 2 provides that the size of the coil interior space is adjustable.

The size adjustment may produce a greater patient coverage with the same SNR as local coils without the size adjustment capability.

The hinging movement of the upper section 2 (e.g., in relation to the lower section) may provide a differentiated height adjustment of the upper section 3 tailored to the anatomy of the patient.

An SNR gain by differentiated height adjustment of the upper section 2 may be provided.

By selecting the position of the hinge 4, a size adjustment that does not occur in parallel and would thus be the same at every point, but occurs in areas, at which a greater adjustment movement is advantageous (e.g., the upper chest area and chin), the upwards movement is at its greatest, is provided. In the area of the forehead and the front of the skull of the patient, where the differences from patient to patient are significantly less, there is the smallest upwards movement.

Surfaces 5, 7 on the hinged joint 4 and a shaft 6 define a specific introduction position for the upper section 2 so that the head coil is as wide open as possible in this position (e.g., to avoid endangering the patient when the upper section 2 is put on).

The coil is configured so that the size is adjusted from the largest to the smallest interior space (e.g., to avoid endangering a patient).

Sprung pressure plates 9 bear the weight of the upper section 2 and prevent the coil swinging down into the closed position. The sprung pressure plates 9 thus maintain the largest possible setting as the initial position.

The interior space may be reduced by slight pressure on the upper section 2.

The angular setting of the saw tooth of the latching bar 8 defines the necessary adjustment force.

At least one sprung locking plate 12 automatically locks the upper section 2.

A latched locking mechanism 8, 12 on both sides creates defined adjustment stages and secures the upper section 2 during the MR examination (e.g., while avoiding vibrations).

The edge of the saw tooth 8 in parallel to the locking plate 12 prevents an undesired opening of the upper section 2 by a force acting from the interior of the coil (e.g., exerted by a patient 105).

A limiting force may be defined via a slight angled position at this edge, through the effects of which the coil may be opened by the patient (e.g., as a panic reaction or emergency unlocking).

A comfortable one-handed operation by actuating the pull handle 14 of the sprung locking plate 12 to open the coil is possible.

Sprung pressure plates 9 allow the upper section 2 to be opened automatically into an initial position.

Stops 15 limit the travel of the locking plate 12 to both sides.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A local coil for a magnetic resonance tomography system, the local coil comprising:
 an upper section and a lower section,
 wherein the upper section is hingeable relative to the lower section around a hinged joint, and
 wherein the hinged joint comprises at least one cutout with introduction surfaces for introducing elements of the upper section into a cutout in a hinge joint of the lower section.

2. The local coil as claimed in claim 1, wherein the upper section is hingeable around a shaft in relation to the lower section.

3. The local coil as claimed in claim 1, wherein the elements of the upper section each have two introduction surfaces.

4. The local coil as claimed in claim 3, wherein the two introduction surfaces are parallel to one another.

5. The local coil as claimed in claim 1, wherein with the hinged joint, after insertion of the elements of the upper section into the hinge joint on the lower section, a shaft of the upper section is rotatable in the hinge joint on the lower section, and
wherein the upper section is pivotable in a direction of the lower section.

6. The local coil as claimed in claim 1, wherein latching bars attached to both sides of the upper section strike against or rest against sprung plates on the lower section.

7. The local coil as claimed in claim 1, further comprising pressure springs that are dimensioned so that a load of the upper section is bearable by the pressure springs.

8. The local coil as claimed in claim 1, wherein latching elements are provided on the upper section, the latching elements each having one or more latching edges, the one or more latching edges in a position of the upper section hinged in a direction of the lower section being latched onto the lower section.

9. The local coil as claimed in claim 8, wherein toothing of the latching edges comprises a saw tooth.

10. The local coil as claimed in claim 9, wherein the latching edges are angled in order to allow emergency unlocking.

11. The local coil as claimed in claim 9, wherein an unlocking element of a locking plate of the lower section is provided in order to release toothing for unlocking.

12. The local coil as claimed in claim 11, wherein movement of the locking plate is limited to both sides by stops.

13. The local coil as claimed in claim 11, wherein the unlocking element comprises a pull handle.

14. The local coil as claimed in claim 8, wherein the latching elements are latching bars.

15. The local coil as claimed in claim 8, wherein the latching edges are each latched onto a locking plate of the lower section.

16. The local coil as claimed in claim 1, wherein the upper section is latchable in a number of positions in relation to the lower section.

17. The local coil as claimed in claim 1, wherein the hinge joint on the lower section is located at (1) a position, in which a local coil placed on a patient is at the greatest distance from feet of the patient, (2) above a head of the patient, or (3) a combination thereof.

18. The local coil as claimed in claim 1, wherein movement on hinging the upper section towards the lower section in an area of a forehead and front of a skull of a patient is smaller than in an area of a chin, a neck, or a combination thereof of the patient.

19. The local coil as claimed in claim 1, wherein the elements of the upper section comprise a stud or a shaft.

20. A local coil for a magnetic resonance tomography system, the local coil comprising:
an upper section and a lower section,
wherein the upper section is hingeable relative to the lower section,
wherein latching bars attached to both sides of the upper section strike against or rest against sprung plates on the lower section,
wherein the latching bars and the sprung plates are configured to lock the upper section in a plurality of positions relative to the lower section, the plurality of positions being different than a closed position.

21. A local coil for a magnetic resonance tomography system, the local coil comprising:
an upper section and a lower section,
wherein the upper section is hingeable relative to the lower section around a hinged joint,
wherein the hinged joint comprises at least one cutout with introduction surfaces for introducing elements of the upper section into a cutout in a hinge joint of the lower section, and
wherein the introduction surfaces, at a cutout of the hinge joint on the lower section, for introduction of pins of the upper section, are at a greater distance from one another than introduction surfaces on elements of the upper section.

22. A local coil for a magnetic resonance tomography system, the local coil comprising:
an upper section and a lower section,
wherein the upper section is hingeable relative to the lower section around a hinged joint,
wherein the hinged joint comprises at least one cutout with introduction surfaces for introducing elements of the upper section into a cutout in a hinge joint of the lower section, and
wherein the introduction surfaces on the cutout in the hinge joint on the lower section are configured for introduction of pins of the upper section, introduction surfaces on elements of the upper section, or a combination thereof, so that the upper section is only placeable on the lower section at a specific angle or within an angular range.

23. The local coil as claimed in claim 22, wherein the upper section is only placeable on the lower section in a wide-open state of the local coil.

* * * * *